United States Patent [19]

Peraita

[11] Patent Number: 5,135,918
[45] Date of Patent: Aug. 4, 1992

[54] METHOD FOR DECREASING REAGINIC ANTIBODY LEVELS

[75] Inventor: Teodoro A. Peraita, Gran Canaria, Spain

[73] Assignee: Broncorp, Ramona, Calif.

[21] Appl. No.: 697,929

[22] Filed: May 2, 1991

Related U.S. Application Data

[63] Continuation of Ser. No. 170,740, Mar. 21, 1988, abandoned.

[51] Int. Cl.$^5$ ............................................. A61K 31/70
[52] U.S. Cl. ........................................ 514/52; 536/25
[58] Field of Search ............................ 514/52; 536/25

[56] References Cited

U.S. PATENT DOCUMENTS

| | | | |
|---|---|---|---|
| 3,160,564 | 12/1964 | Hanus | 514/52 |
| 3,175,948 | 3/1965 | Koff et al. | 514/52 |
| 4,806,354 | 2/1989 | Green | 424/154 |

FOREIGN PATENT DOCUMENTS

| | | |
|---|---|---|
| 3444464 | 1/1986 | Fed. Rep. of Germany. |
| 8606635 | 11/1986 | World Int. Prop. O.. |

OTHER PUBLICATIONS

*The Pharmacological Basis of Therapeutics*, 7th Ed., Goodman et al eds., MacMillan Publishing Co., New York, 1985, pp. 1325–1332.

Dewdney, "Prospects for modulation of the specific immune response in allergic diseases," Ch. 6 in *Allergy and Asthma*, A. B. Kay ed., Blackwell Scientific Publications, London, GB, 1989, pp. 91–98.

Katz, "Suppression of the IgE response with human proteins developed by biotechnology," Ch. 8 in *Allergy and Asthma*, A. B. Kay ed., Blackwell Scientific Publications, London, GB, 1989, pp. 113–125.

Hamberger, R. N. (1975) Science 189: 389.

Caruselli, M. (1952) RIF.MED. 66; 849–851 (informal English translation also attached).

Trampiz, G. (1959) Folia Clinica International, Jul.-Aug. 264–266 (informal English translation also attached).

*Primary Examiner*—John W. Rollins
*Assistant Examiner*—L. Eric Crane
*Attorney, Agent, or Firm*—Knobbe, Martens, Olson & Bear

[57] ABSTRACT

A method for achieving long term relief from the symptoms of atopic allergy, comprising parenteral administration of Vitamin $B_{12}$ to selected patients, is produced. Vitamin $B_{12}$ acts to reduce the levels of reaginic antibody (immunoglobulin) in these patients, and this effect persists beyond the period of treatment. The regimen may include oral administration of Vitamin $B_{12}$ as well as other vitamins.

11 Claims, No Drawings

METHOD FOR DECREASING REAGINIC ANTIBODY LEVELS

The instant application is a continuation of application Ser. No. 07/170,740, filed Mar. 21, 1988 now abandoned.

BACKGROUND OF THE INVENTION

This invention relates to a method for treating certain allergic diseases, primarily those of the upper respiratory tract.

The immune system is capable of responding in a number of effective ways to protect the body from harmful agents such as bacteria, viruses or toxins. In some genetically susceptible individuals who are allergic, it responds inappropriately to innocuous substances. Atopic allergy is expressed as a type I hypersensitivity reaction (Gell and Coombs classification) in which "reaginic" antibodies, usually of the Immunoglobulin E ($I_gE$) class, when triggered by environmental allergens, release chemical mediators such as histamine from the specialized cells to which they are attached. Some of these specialized cells, called "mast" cells, are distributed in the mucous membranes of the upper respiratory system and the gut and also in the skin. Mediators released from tissue mast cells act locally on target organs to produce the distressing symptomatology of hay fever, asthma, food intolerance, or localized itching of the skin (urticaria).

Approximately 10% of the United States population suffers from atopic allergy. Most of the allergens which provoke the hypersensitivity reaction are airborne pollens, animal dander, and common dust, all of which are most likely to enter the body by inhalation to lodge in the respiratory tract. For this reason, allergic rhinitis and allergic bronchial asthma are the most common diseases of their class.

Allergic rhinitis may be seasonal or perennial depending on the causative allergen. Seasonal allergic rhinitis (hay fever) is commonly caused by plant pollens; perennial allergic rhinitis may be caused by agents such as house dust or animal dander. The characteristic feature of allergic rhinitis is the pale edematous swelling of the mucosa of the upper respiratory tract, which may cause obstruction of the nasal passages, sinus ostium and eustachian tubes. Laryngeal edema may also result in hoarseness. Commonly the conjunctiva are swollen and the eyes and nose have a watery discharge.

About one third of the cases of bronchial asthma are allergic in nature, and allergy is a contributing factor in another third. These cases are often described as "extrinsic" asthma. The characteristic feature of bronchial asthma is constriction of bronchial smooth muscle which makes it difficult for the sufferer to move air through the bronchial passages, particularly during exhalation. This constriction in allergic asthma is caused by a response of autonomic nervous system receptors in the bronchial mucosa to the release of histamine and other chemical mediators in response to the allergen stimulation described above.

Drugs can act non-specifically to prevent or relieve the symptoms of hypersensitivity reactions. Cromolyn sodium prevents the release of chemical mediators from tissue mast cells in asthmatic patients, and antihistamine drops are used to competitively inhibit this mediator effectively after its release and so alleviate the symptoms of rhinitis. Beta-adrenergic agents are used as bronchodilators for asthma, and steroids relieve the bronchial constriction by an unknown mechanism of action.

Specific treatment of atopic allergy requires prior identification of the offending allergen. Skin testing, in which a small quantity of allergen scratched or injected into the skin produces a characteristic wheal and flare in an allergic individual, has historically been the method of choice in allergen identification; however, it is now being replaced by more convenient in vitro immunoassays for specific $I_gE$ antibodies. Both skin testing and specific $I_gE$ assays are useful when the patient is sensitive to a common allergen, but in cases where the allergen is uncommon, the search to identify it by either procedure may be tedious, expensive, and in some instances, impossible.

If the specific allergen can be identified, future allergic episodes can be prevented by eliminating it from the patient's environment. If this is restrictive or not possible, and the allergy is incapacitating, the patient may elect to be specifically desensitized to the allergen by immunotherapy. To achieve this, small amounts of extracted allergen and/or chemically denatured allergen (allergoid) are injected into the patient repeatedly over a period of time. The allergoid should be incapable of stimulating $I_gE$ production but instead stimulate a "blocking" $I_gG$. $I_gG$ binds allergen in a soluble complex and thus prevents its interaction with $I_gE$ on the surface of tissue mast cells. Where it is successful, this alteration of the immerse response produces long-lasting relief. Desensitization is less feasible when, as often is the case, a patient is sensitive to multiple allergens. Also, it carries the risk of triggering an allergic incident, requires an extended period of time to be effective, and frequently fails altogether to protect against the allergic response.

A desirable treatment for atopic allergy would be one that could achieve the long lasting benefits of desensitization immunotherapy, and yet like the drug approach, not require an identification of specific allergen(s).

A non-specific immunotherapy for atopic allergy was proposed by R. Hamburger in 1975 (Science 189 389). In this approach, it was suggested that a synthetic pentapeptide, identical to that region of the $I_gE$ molecule which binds to the $I_gE$ receptor on the mast cell surface, would be injected into the patient. This peptide could then block $I_gE$ attachment by competing for the binding site on mast cell surfaces, and thus prevent the release of chemical mediators triggered by allergen. Successful results have been reported when the serum of allergic patients treated with appropriate pentapeptide showed decreased $I_gE$ level as measured by the Prausnitz-Kustner reaction; however, this mode of therapy is not yet available.

Vitamin $B_{12}$ is a specific therapy only in pernicious anemia or in specific nutritional deficiency; however, it is commonly used as a non-specific, supportive therapy for patients recovering from infections, complaining of fatigue, or experiencing physiological stress from various and diverse causes. Not surprisingly, it has been similarly administered to patients suffering from asthma. In a few cases, these patients experienced short term relief from their symptoms together with subjective qualitative feelings of well-being; but overall, the efficacy of vitamin $B_{12}$ therapy as a general remedy for atopic allergy is indeterminate.

In 1952, Caruselli reported a one year experimental use of vitamin $B_{12}$ injections in attempting to relieve the symptoms of eight asthmatic patients who were refractory to conventional drugs. He reports that seven of these obtained temporary symptomatic relief after five to twenty days of treatment. The other patient showed no improvement after three months of treatment with 30 µg of vitamin B$_{12}$ per day.

Caruselli's study was defective because it reports no control group studied which could provide data on the number of patients who improved without treatment. Further, the study does not indicate whether the asthma cases treated were of the extrinsic or intrinsic type, and if extrinsic, whether the underlying allergy was seasonal, in which case symptoms could disappear spontaneously; nor does he indicate that other medication was discontinued during the B$_{12}$ treatment. Finally, the study is ambiguous and inconclusive because the patients were not followed long enough to determine if the symptomatic relief persisted beyond the period of treatment.

In 1959, Trampiz undertook a clinical study of Vitamin B$_{12}$ therapy in a group of 14 adults and 50 children. Again, there were no controls, no classification into disease categories, and no long-term follow up. The dosages between the adult and child groups were disproportionate, with the children receiving 30 µg per day for 20 days and the adults 4 to 5 mg. Of the 64 patients treated, 42 showed some degree of improvement, and the remainder were unresponsive. All of those who responded were children who were poorly nourished at the beginning of treatment, and their symptomatic relief occurred in the context of better appetite and improved nutrition. The adults, none of whom enjoyed symptomatic relief from asthma, gained weight and felt better.

It is accordingly an object of this invention to provide a method for treating atopic allergy by selecting from the patient population a group of individuals likely to benefit from Vitamin B$_{12}$ therapy, and applying such therapy to provide these patients with long term relief from these diseases.

It is a further object of this invention to provide a method for treating atopic allergy non-specifically, that is without the need to identify a causative antigen, by using an immunotherapy approach which provides long-term relief comparable to that of specific desensitization.

BRIEF SUMMARY OF THE INVENTION

I have discovered a simple, safe and effective method for providing long-term relief to those patients suffering from atopic allergies, especially allergic rhinitis and allergic asthma, who have elevated levels of reaginic antibody, immunoglobulin E (I$_g$E), in the bloodstream.

The method comprises first, identifying those patients who can be successfully treated by determining the level of I$_g$E in the blood of patients who have experienced symptoms of these allergies, and selecting those having elevated blood levels for treatment. The level of I$_g$E antibodies in the blood of the selected group of patients is then reduced by the parenteral administration of an effective dose of a chemical species having the coenzyme activity of vitamin B$_{12}$ at repeated, regular intervals so as to maintain an elevated level of vitamin B12 activity in the blood for a period of time sufficient to substantially reduce the level of I$_g$E in the patient's tissues, and in so doing, eliminate the agent of the allergic response.

Vitamin B$_{12}$ is administered parenterally as cyanocobalamin which may be substituted with alkyl groups, such as methyl or ethyl, or with hydroxyl groups. In a preferred method, the vitamin is cyanocobalamin. The substance is dissolved in a convenient volume of an aqueous solution, such as distilled H$_2$O or physiological saline, and administered in doses of from about 5 to 50 µg, at intervals of 24 hours or less for from about 3 to 45 days. Injection may be made subcutaneously or intramuscularly. In a preferred embodiment, 15 µg of cyanocobalamin in 1 cc of distilled water is administered subcutaneously every 12 hours for 15 days. In another embodiment of this method, the parenteral injection of vitamin B$_{12}$ is combined with the oral administration of the B complex vitamins B$_1$, B$_6$ and B$_{12}$, and vitamin C. The B complex vitamins are administered in doses of between approximately 50 and 200 mg B$_1$, between approximately 50 and 500 mg B$_6$, and between approximately 10 µg and 2 mg B$_{12}$; vitamin C is administered in a dose of between approximately 1 and 10 grams. In a preferred embodiment the B complex vitamins are administered together twice a day and vitamin C is administered once a day at least two hours before or after the time the B complex vitamins are given. In a particularly preferred embodiment, doses of 100 mg of B$_1$, 250 mg of B$_6$ and 1 mg of B$_{12}$ are administered together orally twice a day and a dose of 4 gm of vitamin C is administered once a day at least two hours before or after the B complex vitamins. The oral administration of these vitamins is continued throughout the course of the parenteral vitamin B$_{12}$ treatment.

In yet another embodiment the parenteral therapy with vitamin B$_{12}$ is applied either alone or in combination with the oral administration of B complex vitamins and vitamin C in the therapy of allergic rhinitis or allergic bronchial asthma. In yet another embodiment of the invention, the effectiveness of the foregoing therapies is monitored by sequential determinations of the concentration of total or specific I$_g$E in the blood. In a particularly preferred embodiment, the use of the therapy for allergic bronchial asthma is monitored by at least two pulmonary function tests. The first in the series of either monitoring tests should be done before the beginning of treatment, as a baseline.

These and other advantages and features of the present invention will become more fully apparent from the following description, examples, and appended claims.

DETAILED DESCRIPTION OF THE INVENTION

The parenteral administration of a cyanocobalamin compound having the general structure and coenzyme activity of vitamin B$_{12}$ is capable of reducing the serum levels of reaginic antibody, I$_g$E, found in many patients suffering from allergic disorders, thereby providing these patients with long term relief from their symptoms.

Patients who are likely to benefit from the therapy are those who have experienced allergic attacks of rhinitis or extrinsic asthma, and whose serum levels of I$_g$E are significantly above normal. These patients may accordingly be identified by medical history and by a quantitative determination of total non-specific I$_g$E levels by a immunoassay procedure, such as Phadezym I$_g$E Prist. The level of I$_g$E response to a specific allergen, where that allergen is known, may be determined by a corresponding RAST immunoassay (Pharmacia, Piscataway, N.J.). Specific I$_g$E levels may also be qualitatively demonstrated by the "wheal and flare" response of conventional skin testing. Patients suffering from allergic bronchial asthma may receive a collateral pulmonary function test (PLF).

The primary therapeutic agent is cyanocobalamin or any of its derivatives or analogs having the coenzyme activity of Vitamin $B_{12}$. Hydroxy-cyanocobalamin has the advantage of being less rapidly excreted in the urine than other species. Treatment by injection is essential; oral administration of vitamin $B_{12}$ alone has been found to be ineffective. In a preferred regimen, vitamin $B_{12}$, as cyanocobalamin, is administered subcutaneously at a dose of 15 μg, in a volume of 1 cc, every 12 hours for 15 consecutive days. The dose may be in the range of from about 5 to 50 μg, and the duration of treatment from about 3 to 45 days. The two daily doses may also be administered at an 8 hour interval.

In an alternate embodiment of the invention, the parenteral vitamin $B_{12}$ therapy is combined with the oral administration of B complex vitamins $B_1$, $B_6$, and $B_{12}$ as well as vitamin C. The B complex vitamins are given in doses of 50 to 200 mg $B_1$, 50 to 500 mg $B_6$, and 10 μg to 2 mg $B_{12}$, vitamin C is given in a dose of from 1 to 10 gm. In a preferred embodiment, 100 mg of $B_1$, 250 mg of $B_6$ and 1 mg of $B_{12}$ are taken orally twice daily, and 4 grams of vitamin C are taken once daily, at least two hours before or after the B complex are separated in order to prevent a destructive action of vitamin C on the B complex.

When the injections are supplemented with oral doses of vitamins the treatment is effective in a larger proportion of patients and the relief from symptoms more long-lasting. Therapy of patients is monitored by the PRIST and RAST tests as well as PLF studies. Therapy is most effective if it is begun while patients are asymptomatic; however, if symptoms appear during the course of treatment, they may be treated by conventional methods and the vitamin therapy need not be interrupted.

Parenteral low level vitamin $B_{12}$ therapy are conventionally employed as a specific treatment for pernicious anemia. However pernicious anemia and atopic allergy are distinct in pathogenesis and the mechanism by which vitamin $B_{12}$ alleviates symptoms in each disease is likewise distinct.

Pernicious anemia results from a lack of sufficient "intrinsic factor" in the intestine to allow absorption of vitamin $B_{12}$. It results not only in anemia, but also digestive disorders and neurologic damage. Intramuscular injections of vitamin $B_{12}$ of 1 μg or more daily provoke a rapid response, with new blood cell formation (reticulocytosis) apparent in a few days. Because of the intrinsic factor defect, injections of about 100 μg must be given every month for an indefinite period.

Atopic allergy, by contrast, is caused by a disorder in the immune system, resulting in the inappropriate reaginic response to harmless agents. Vitamin $B_{12}$, in the mode of therapy defined in this invention, acts to correct this disorder so as to give long lasting relief of symptoms, if not a cure. The administration of Vitamin $B_{12}$ need not be continued indefinitely to achieve the result.

The mechanism by which Vitamin $B_{12}$ receives atopic allergy is uncertain, but a reasonable hypothesis may be constructed. Vitamin $B_{12}$ is known to be essential to human nutrition, and its deficiency particularly affects the nervous system, resulting in degenerative changes and gross disorders in function.

The inappropriate immune response of atopic allergy has been experimentally linked to an imbalance in the function of the autonomic nervous system. Animals which lack the ability to demonstrate anaphylaxis, an extreme manifestation of allergy, can be induced to this hypersensitive state by using agents that block the action of one branch of this system, preventing a beta-adrenergic response. Consequently the sympathetic (beta-adrenergic) and parasympathetic (cholinergic) systems become unbalanced when beta-adrenergic blockade occurs, and antibody formation also shifts from normal $I_gG$ and $I_gM$ synthesis to that of $I_gE$.

Human asthma patients respond with symptomatic relief to drugs such as metaproterenal, which enhance betaadrenergic response. An autonomic imbalance with betaadrenergic defect, overactive cholinergic control, and elevated $I_gE$ levels (similar to the condition induced in laboratory animals) could result in disturbed homeostatic control of adrenergic receptors controlling the smooth muscles of the bronchi. Conceivably the mechanism of effective vitamin $B_{12}$ therapy in extrinsic asthma involves a restoration of normal homeostasis of the autonomic nervous system.

A more complete understanding of the invention can be obtained by referring to the following example, which is not intended, however, to limit the invention.

A group of ten patients were selected for study from a population of those with a history of allergic rhinitis or allergic bronchial asthma. On the basis of screening tests for specific and non-specific $I_gE$, it was determined that each patient selected had levels of either or both of these types of reaginic antibodies substantially above the normal range.

In this group of ten patients, seven (FL, IL, EM, JM, PR, MT and JU) were asthmatic; two (TC and AR) had suffered from rhinitis and bronchitis with bronchospasm; one (AA) suffered from perennial allergic rhinitis. Specific allergies were known for five of the patients (AA, IL, EM, PR and MT). Both EM and MT had previously undergone desensitization therapy.

All patients were treated with two subcutaneous injections of vitamin $B_{12}$ per day, as 15 μg of cyanocobalamin (natural extract of calves liver) in 1 cc. of distilled water. Injections were given for a period of 15 days. Five of the patients (AA, IL, EM, PR and JU) were given supplemental doses of vitamin $B_{12}$ and 4 grams of vitamin C daily during the couse of treatment.

Table 1 shows the immunoassay results for nonspecific and specific $I_gE$ levels in these patients before and after therapy. All patients showed significant reduction in $I_gE$ levels following therapy. The table also includes non-specific $I_gE$ levels of two patients, HA (66 year old male) and GA (67 year old female) who had been lifelong sufferers from these types of allergies until they underwent this therapy in Spain in 1977. Since that time they have been symptom free. The PRIST total $I_gE$ levels for these two patients are in the normal range. In Table 2, pulmonary function studies for FL show that the moderate airway obstruction existing before the treatment was eliminated and a normal breathing pattern restored.

TABLE 1

RESPONSE OF PATIENTS TO VITAMIN $B_{12}$ IMMUNOTHERAPY AS DETERMINED BY ASSAYS FOR SERUM LEVELS OF IMMUNOGLOBULIN

| PATIENT | SEX/AGE | $I_eE$ PRIST 0 | 1 | 2 | 3 | | $I_eE$ RAST 0 | 1 | 2 |
|---|---|---|---|---|---|---|---|---|---|
| AA | F42 | 650 | 325 | 310 | 160 | g × 2 | — | 0.8 | 2.0 |
|    |     |     |     |     |     | w × 1 | — | 1.33 | — |
|    |     |     |     |     |     | h × 2 | 3.0 | 2.0 | — |
|    |     |     |     |     |     | e × 1 | 0.66 | — | 0.66 |
|    |     |     |     |     |     | t × 3 | — | 7.0 | 1.66 |
| TC | F21 | 850 | 400 | 430 | 491 | g × 2 | — | — | — |
|    |     |     |     |     |     | w × 1 | 1.08 | — | — |
|    |     |     |     |     |     | h × 2 | 78 | 70 | 8.28 |
|    |     |     |     |     |     | e × 1 | 0.33 | 0.66 | — |
|    |     |     |     |     |     | t × 3 | 5.0 | 2.0 | — |
| FL | M73 | 430 | 190 | | | g × 2 | 2.0 | — | |
|    |     |     |     |     |     | w × 1 | 1.83 | — | |
|    |     |     |     |     |     | h × 2 | 4.0 | — | |
|    |     |     |     |     |     | e × 1 | — | | |
|    |     |     |     |     |     | t × 3 | 2.0 | — | |
| IL | F23 | 90 | 65 | | | g × 2 | 0.8 | — | |
|    |     |     |     |     |     | w × 1 | 0.66 | 0.66 | |
|    |     |     |     |     |     | h × 2 | — | 0.57 | |
|    |     |     |     |     |     | e × 1 | 2.0 | 0.33 | |
|    |     |     |     |     |     | t × 3 | 0.33 | 0.33 | |
| EM | F43 | 60 | 67.5 | | | g × 2 | — | — | |
|    |     |     |     |     |     | w × 1 | 1.33 | — | |
|    |     |     |     |     |     | h × 2 | 3.71 | — | |
|    |     |     |     |     |     | e × 1 | 1.33 | — | |
|    |     |     |     |     |     | t × 3 | — | — | |
| JM | M31 | 300 | 375 | 145 | | g × 2 | — | 0.4 | |
|    |     |     |     |     |     | w × 1 | — | — | |
|    |     |     |     |     |     | h × 2 | 8.0 | 6.0 | |
|    |     |     |     |     |     | e × 1 | 2.0 | 1.0 | |
|    |     |     |     |     |     | t × 3 | — | 5.5 | |
| AR | M59 | 1300 | 450 | | 263 | g × 2 | 1.2 | 1.8 | |
|    |     |     |     |     |     | w × 1 | 0.33 | — | |
|    |     |     |     |     |     | h × 2 | — | 10 | |
|    |     |     |     |     |     | e × 1 | — | — | |
|    |     |     |     |     |     | t × 3 | — | 2 | |
| PR | F29 | 950 | 425 | | | g × 2 | 2.0 | 2.2 | |
|    |     |     |     |     |     | w × 1 | 0.83 | 1.66 | |
|    |     |     |     |     |     | h × 2 | 16.28 | 18.28 | |
|    |     |     |     |     |     | e × 1 | 0.66 | 1.33 | |
|    |     |     |     |     |     | t × 3 | — | 1.0 | |
| MT* | F35 | 230 | 135 | 95 | 93 | g × 2 | — | — | — |
|    |     |     |     |     |     | w × 1 | — | — | — |
|    |     |     |     |     |     | h × 2 | 4.0 | 10.0 | 1.14 |
|    |     |     |     |     |     | e × 1 | — | 1.0 | — |
|    |     |     |     |     |     | t × 3 | — | 2.0 | 0.33 |
| JU | F65 | 30 | 60 | | | g × 2 | 1.2 | — | |
|    |     |     |     |     |     | w × 1 | 1.0 | 0.66 | |
|    |     |     |     |     |     | h × 2 | 0.57 | — | |
|    |     |     |     |     |     | e × 1 | — | 1.0 | |
|    |     |     |     |     |     | t × 3 | 0.66 | — | |
| LONG TERM SYMPTOM-FREE PATIENTS | | | | | | | | | |
| HA | M66 | | 70 | | | g × 2 | — | | |
|    |     |     |     |     |     | w × 1 | — | | |
|    |     |     |     |     |     | h × 2 | — | | |
|    |     |     |     |     |     | e × 1 | 1.0 | | |
|    |     |     |     |     |     | t × 3 | 2.0 | | |
| GA | F | | 57.5 | | | g × 2 | — | | |
|    |     |     |     |     |     | w × 1 | — | | |
|    |     |     |     |     |     | h × 2 | — | | |
|    |     |     |     |     |     | e × 1 | — | | |
|    |     |     |     |     |     | t × 3 | — | | |

*(Pt experienced ASTHMA attack on day 15 of treatment)
"0" determinations before initial treatment;
"1" = 14–21 days later;
"2" = 45–60 days later;
"3" = 150 days later
PRIST TEST: Values are in KU/L

|  |  |  | Mean | I.S.D. | 2.S.D. |
|---|---|---|---|---|---|
| Normal | age | 31–50 years | 19 | 79 | 324 |
| ranges, | | 51–80 years | 12 | 48 | 197 |

RAST TEST: Values are in PRU/ML
Normal value: not detected (—).
Allergen-specific control = 2PRU/ML.
g × 2 = grass pollen
w × 2 = weed pollen
h × 2 = house dust

TABLE 1-continued
RESPONSE OF PATIENTS TO VITAMIN $B_{12}$ IMMUNOTHERAPY AS DETERMINED BY ASSAYS FOR SERUM LEVELS OF IMMUNOGLOBULIN

| PATIENT | SEX/AGE | $I_gE$ PRIST | | | | $I_gE$ RAST | | |
|---|---|---|---|---|---|---|---|---|
| | | 0 | 1 | 2 | 3 | 0 | 1 | 2 | e × 1 = animal dander
t × 3 = tree pollen

TABLE 2

| SPIROMETRY | | PREBRONCHODILATOR | | POSTBRONCHODILATOR | | | |
|---|---|---|---|---|---|---|---|
| | | ACTUAL | PRED. | PRE-DICATED | ACTUAL | % PRED. | % CHANGE |
| | | PRE-TREATMENT | | | | | |
| FV | (LITERS) | 1.93 | 57 | 3.37 | 3.02 | 90 | 57 |
| FEV-1 | (LITERS) | 1.57 | 58 | 2.70 | 2.29 | 85 | 46 |
| FEV-1/FVC | (%) | .82 | | .79 | .76 | | −7 |
| FEF25-75 | (L/SEC) | 1.40 | 52 | 2.70 | 1.84 | 68 | 32 |
| PEFR | (L/SEC) | 4.94 | 66 | 7.45 | 6.53 | 88 | 32 |
| FEF25 | (L/SEC) | 2.63 | 39 | 6.80 | 5.09 | 75 | 94 |
| FEF50 | (L/SEC) | 1.50 | 44 | 3.42 | 2.30 | 67 | 54 |
| FEF75 | (L/SEC) | .69 | 61 | 1.13 | .55 | 48 | 21 |
| "Moderate airway obstruction" | | | | | | | |
| | | POST-TREATMENT | | | | | |
| FVC | (LITERS) | 3.30 | 95 | 3.47 | 3.55 | 102 | 8 |
| FEV-1 | (LITERS) | 2.38 | 86 | 2.78 | 2.57 | 92 | 8 |
| FEV-1/FVC | (%) | .72 | | .79 | .72 | | 0 |
| FEF25-75 | (L/SEC) | 1.66 | 60 | 2.77 | 1.76 | 63 | 6 |
| PEFR | (L/SEC) | 8.93 | 118 | 7.57 | 8.41 | 111 | −6 |
| FEF25 | (L/SEC) | 3.57 | 52 | 6.91 | 4.71 | 68 | 32 |
| FEF50 | (L/SEC) | 2.07 | 59 | 3.50 | 2.03 | 58 | −2 |
| FEF75 | (L/SEC) | .56 | 48 | 1.17 | .58 | 49 | 3 |

"Normal spirometry"

The invention may be embodied in other specific forms without departing from its spirit or essential characteristics. The described embodiments, therefore, are to be considered in all respects only as illustrative and not restrictive. All changes which come within the meaning and range of equivalency of the claims are to be embraced with their scope.

What is claimed is:

1. A method for treating atopic allergy in humans, comprising:
   selecting a human having a level of reaginic antibodies in the blood substantially above the normal range as a subject for treatment;
   parenterally administering to said human an effective, allergy-opposing amount of Vitamin $B_{12}$, to substantially reduce said level of reaginic antibodies.

2. A method according to claim 1, wherein said Vitamin $B_{12}$ is cyanocobalamin.

3. A method according to claim 1 or 2, wherein said amount of Vitamin $B_{12}$ is administered in doses of between approximately 5 μg to 50 μg.

4. A method according to claim 3, wherein said dose is administered at intervals of 24 hours or less.

5. A method according to claim 3, wherein said dose is administered at said intervals for a period of approximately 3 to 45 days.

6. A method according to claim 1 or 2, wherein said dose is about 15 μg and is administered about every 12 hours for approximately 15 days.

7. A method according to claim 1 or 2, wherein said chemical species is in aqueous solution.

8. A method according to claim 7, wherein said solution is injected subcutaneously.

9. A method according to claim 7, wherein said solution is injected intramuscularly.

10. A method according to claim 1, applied in the therapy of allergic bronchial asthma.

11. A method according to claim 1, applied in the therapy of allergic rhinitis.